United States Patent [19]

Adolf

[11] Patent Number: 5,582,998
[45] Date of Patent: Dec. 10, 1996

[54] MONOCLONAL ANTIBODIES AGAINST HUMAN TNF-BINDING PROTEIN I (TNF-BP I) AND IMMUNOASSAYS THEREFOR

[75] Inventor: Günther Adolf, Vienna, Austria

[73] Assignee: Boehringer Ingelheim International GmbH, Ingelheim am Rhein, Germany

[21] Appl. No.: 365,161

[22] Filed: Dec. 28, 1994

Related U.S. Application Data

[63] Continuation of Ser. No. 167,866, filed as PCT/EP92/01335, Jun. 13, 1992, abandoned.

[30] Foreign Application Priority Data

| Jun. 19, 1991 | [DE] | Germany | 41 20 213.9 |
| Jan. 3, 1992 | [DE] | Germany | 42 00 049.1 |

[51] Int. Cl.$^6$ .................... G01N 33/53; G01N 33/537; C07K 16/18
[52] U.S. Cl. .................. 435/7.1; 435/7.92; 435/7.94; 435/70.21; 435/240.27; 436/811; 436/815; 530/388.1
[58] Field of Search .................. 435/7.1, 7.21, 435/7.23, 7.32, 7.92, 7.94, 240.27, 70.21; 436/815, 811; 530/388.1

[56] References Cited

FOREIGN PATENT DOCUMENTS

| 0308378 | 3/1989 | European Pat. Off. . |
| 0334165 | 9/1989 | European Pat. Off. . |
| 0412486 | 2/1991 | European Pat. Off. . |

OTHER PUBLICATIONS

Adolf et al, "A monoclonal antibody-based enzyme immunoassay for quantitation of human tumor necrosis factor binding protein I, a soluble fragment of the 60 kDa receptor, in biological fluids", J. Immunol. Methods, 143:127–136 (Sep. 20, 1991).
Voller et al, "Enzyme–Linked Immunosorbent Assay", pp. 99–109 in Manual of Clinical Immunology, (American Society for Microbiology, Washington, D.C.) 1986.
Thoma et al., "Identification of a 60–kD Tumor Necrosis Factor (TNF) Receptor as the Major Signal Transducing Component in TNF Responses," J. Exp. Med. 172:1019–1023 (Oct. 1990).
Beutler, B., "The Presence of Cachectin/Tumor Necrosis Factor in Human Disease States," Am. J. Med. 85:287–288 (Sep. 1988).
Beutler & Cerami, "The Biology of Cachectin/TNF—A Primary Mediator of the Host Response," Ann. Rev. Immunol. 7:625–655 (1989).
Brockhaus et al., "Identification of two types of tumor necrosis factor receptors on human cell lines by monoclonal antibodies," Proc. Natl. Acad. Sci. USA 87:3127–3131 (Apr. 1990).
Engelmann et al., "A Tumor Necrosis Factor–binding Protein Purified to Homogeneity from Human Urine Protects Cells from Tumor Necrosis Factor Toxicity," J. Biol. Chem. 264:11974–11980 (Jul. 15, 1989).
Engelmann et al., "Two Tumor Necrosis Factor–binding Proteins Purified from Human Urine: Evidence for Immunological Cross–Reactivity with Cell Surface Tumor Necrosis Factor Receptors," J. Biol. Chem. 265:1531–1536 (Jan. 25, 1990).
Engelmann et al., "Antibodies to a Soluble Form of a Tumor Necrosis Factor (TNF) Receptor Have TNF–like Activity," J. Biol. Chem. 265:14497–14504 (Aug. 25, 1990).
Gray et al., "Cloning and expression of cDNA for human lymphotoxin, a lymphokine with tumour necrosis activity," Nature 312:721–724 (Dec. 27, 1984).
Himmler et al., "Molecular Cloning and Expression of Human and Rat Tumor Necrosis Factor Receptor Chain (p60) and Its Soluble Derivative, Tumor Necrosis Factor–Binding Protein," DNA and Cell Biol. 9:705–715 (1990).
Kohno et al., "A second tumor necrosis factor receptor gene product can shed a naturally occurring tumor necrosis factor inhibitor," Proc. Natl. Acad. Sci. USA 87:8331–8335 (Nov. 1990).
Kramer & Carver, "Serum–free in vitro bioassay for the detection of tumor necrosis factor," J. Immunol. Meth. 93:201–206 (1986).
Lähdevirta et al., "Elevated Levels of Circulating Cachectin/Tumor Necrosis Factor in Patients with Acquired Immunodeficiency Syndrome," Am. J. Med. 85:289–291 (Sep. 1988).
Lantz et al., "Infusion Of Tumor Necrosis Factor (TNF) Causes An Increase In Circulating TNF–Binding Protein In Humans, " Cytokine 2:402–406 (Nov. 1990).
Lantz et al., "Characterization In Vitro of a Human Tumor Necrosis Factor–binding Protein: A Soluble Form of a Tumor Necrosis Factor Receptor," J. Clin. Invest. 86:1396–1402 Nov. 1990.
Loetscher et al., "Molecular Cloning and Expression of the Human 55 kd Tumor Necrosis Factor Receptor," Cell 61:351–359 (Apr. 20, 1990).
Loetscher et al., "Recombinant 55–kDa Tumor Necrosis Factor (TNF) Receptor: Stoichiometry of Binding to TNFα and TNFβ and Inhibition of TNF Activity," J. Biol. Chem. 266:18324–18329 (Sep. 25, 1991).

(List continued on next page.)

*Primary Examiner*—Paula K. Hutzell
*Assistant Examiner*—Patricia A. Duffy
*Attorney, Agent, or Firm*—Sterne, Kessler, Goldstein & Fox, P.L.L.C.

[57] ABSTRACT

The invention concerns monoclonal antibodies, designated tbp-1, tbp-2 and tbp-6, against the extracellular part of the human 60 kD TN tumour necrosis factor receptor (TNF-BP I). These antibodies are suitable for use in highly sensitive immuno-assays for demonstrating the presence of TNF-BP I in body fluids, including urine, and in cell-culture residues. The determination of the TNF-BP I concentration as the basis for a diagnosis of pathological conditions associated with activation of the TNF receptor system is thus particularly useful if the α-TNF concentration in the organism falls more rapidly than the TNF-BP I concentration. In addition, tbp-1 and tbp-6 can be used to strengthen the protective action of TNF-BP I against α-TNF and/or β-TNF.

27 Claims, 5 Drawing Sheets

OTHER PUBLICATIONS

Michie et al., "Detection of circulating tumor necrosis factor after endotoxin administration," *New Engl. J. Med.* 318:1481–1486 (Jun. 9, 1988).

Offner et al., "Serum tumor necrosis factor levels in patients with infectious disease and septic shock," *J. Lab. Clin. Med.* 116:100–105 (Jul. 1990).

Olsson et al., "Isolation and characterization of a tumor necrosis factor binding protein from urine," *Eur. J. Haematol.* 42:270–275 (1989).

Paul & Ruddle, "Lymphotoxin," *Ann. Rev. Immunol.* 6:407–438 (1988).

Peetre et al., "A tumor necrosis factor binding protein is present in human biological fluids," *Eur. J. Haematol.* 41:414–419 (1988).

Pennica et al., "Human tumour necrosis factor: precursor structure, expression and homology to lymphotoxin," *Nature* 312:724–729 (Dec. 27, 1984).

Schall et al., "Molecular Cloning and Expression of a Receptor for Human Tumor Necrosis Factor," *Cell* 61:361–370 (Apr. 20, 1990).

Seckinger et al., "A Human Inhibitor of Tumor Necrosis Factor α," *J. Exp. Med.* 167:1511–1516 (Apr. 1988).

Smith et al., "A Receptor for Tumor Necrosis Factor Defines an Unusual Family of Cellular and Viral Proteins," *Science* 248:1019–1023 (May 25, 1990).

MONOCLONAL ANTIBODIES AGAINST HUMAN TNF-BINDING PROTEIN I (TNF-BP I) AND IMMUNOASSAYS THEREFOR

This application is a continuation of application Ser. No. 08/167,866, filed as PCT/EP92/01335, Jun. 13, 1992, now abandoned.

FIELD OF THE INVENTION

The present invention relates to monoclonal antibodies against the TNF-binding protein I (TNF-BP I) and to hybridoma cell lines which secrete them.

BACKGROUND OF THE INVENTION

The two structurally related cytokines tumour necrosis factor (TNF-α) and lymphotoxin (TNF-β) were originally discovered as a result of their cytotoxic in vitro activity against tumour cells and their ability to induce haemorrhagic necroses of tumours in a mouse model. The cloning of their cDNAs and their expression in *E. coli* have made these proteins available in virtually unlimited quantities and have made it possible to develop highly specific antibodies and sensitive immunoassays. There is a wealth of information on the biological activities of these proteins, their physiological roles as pleotropic mediators of inflammatory processes and their participation in pathological conditions. In particular, an increased production of TNF-α has been linked with the pathogenesis of, for example, septic shock, tissue damage in the "Graft-versus-host" disease and cerebral malaria and cachexia (Beutler, 1988; Paul and Ruddle, 1988; Beutler and Cerami, 1989).

The possible undesirable effects of TNF-α have led to a search for natural inhibitors of this cytokine. A protein which binds to TNF-α and thereby inhibits the activity thereof was originally identified in the urine of patients with kidney failure (Peetre et al., 1988) and fever patients (Seckinger et al., 1988). This protein with an apparent molecular weight of about 30 kDa was purified in order to homogenise it, partially sequenced (EP-A2 308 378) and the cDNA was cloned (Olsson et al., 1989; Engelmann et al., 1989; Himmler et al., 1990; Schall et al., 1990). The structure of the cDNA showed that this protein, designated TNF-BP, is the extracellular fragment of a TNF receptor (TNF-R). (It was assumed that this fragment is released by proteolytic cleaving.) These results were confirmed by isolation of the intact membrane receptor for TNF-α, which was carried out independently by other working groups (Loetscher et al., 1990). The entire receptor protein consists of 455 amino acids (55–60 kDa); TNF-BP makes up the majority of the extracellular domain of the receptor and contains all three N-glycosylation sites. It was found that TNF-BP isolated from urine is heterogeneous at the N-terminus as a result of proteolytic cleaving and is therefore a mixture of two molecular forms consisting of 161 amino acids (main fraction) or 172 amino acids (Himmler et al., 1990). Recently, the existence of a second TNF-binding protein was demonstrated, which is a fragment of a second TNF receptor type having a higher molecular weight (75–80 kDa; Engelmann et al., 1990a; Smith et al., 1990; Kohno et al., 1990). The two receptors and binding proteins were then designated TNF-R I/TNF-BP I and TNF-R II/TNF-BP II (for the 60 kDa and 80 kDa receptors, respectively). Sequence comparison showed that the two proteins are structurally related; in particular, the number and distribution of the cysteine groups is very similar. However, the two receptors differ from each other immunologically (Engelmann et al., 1990a; Brockhaus et al., 1990).

The human 60 kDa TNF-receptor plays an essential part in TNFα-signal transmission. The activity of the receptor is subjected to several regulatory effects on a protein basis: the treatment of cells with phorbol esters or other activators of protein kinase C results in a rapid decrease in the number of cellular binding sites for TNF-α. This is linked with the release of the extracellular part of the receptor, corresponding to TNF-BP I, by proteolytic cleaving. Similar effects, albeit with different kinetics, are caused by various other substances, particularly by the physiological ligands TNF-α and TNF-β. The cleavage sites for the protease on human and rat TNF-R I are conserved; they differ in structure from the specificity of all known proteases. It is therefore probable that a highly specific proteolytic enzyme is part of a regulating circuit which controls the sensitivity of cells to TNFs; the exact mechanism of these events is not yet known. Recently this phenomenon has also been observed in vivo: it was found that the administration of TNF-α to cancer patients resulted in a significant increase of TNF-BP I in the serum (Lantz et al., 1990a).

The concentration of TNF-BP I in culture residues or body fluids is therefore an indicator of the activation of the TNF receptor system in vitro or in vivo as a result of interactions with the ligands or transmodulation by other mediators; the TNF-BP I concentration in body fluids can thus be regarded as a useful marker for various diseases.

There was therefore a need for efficient and sensitive methods of detecting TNF-BP I and for kits which can be used for such detection methods.

Monoclonal antibodies against TNF-R I have been described which were prepared by immunising with the solubilised receptor (Brockhaus et al., 1990; EP A2 334 165; Thoma et al., 1990) or with purified TNF-BP I (Engelmann et al., 1990b); however, it was not shown that the antibodies are suitable for use in immunoassays for TNF-BP I.

Lantz et al. (1990a) have developed a competitive ELISA in which, in a three-step test method, test plates coated with TNF-BP I, polyclonal rabbit antibodies against TNF-BP I, biotin-labelled goat antibodies against rabbit immunoglobulin and avidin-coupled alkaline phosphatase were used. By means of this assay, the presence of TNF-BP I in serum from normal donors was detected and increased concentrations of TNF-BP I were detected in sera from patients suffering from kidney failure or cancer patients who had been treated with TNF-α.

EP A1 412 486 describes monoclonal antibodies against TNF-BP I. One of these antibodies was used in a sandwich ELISA as a coating antibody: polyclonal rabbit anti-TNF-BP I antibody was used as the second antibody and polyclonal goat anti-rabbit antibody was used as the third, enzyme-coupled antibody.

The known assays are complicated in their structure and procedure required and moreover the use of polyclonal antibodies involves the use of animals, which is something which is increasingly to be avoided.

SUMMARY OF THE INVENTION

The present invention relates to monoclonal antibodies (tbp-1, tbp-2, and tbp-6) directed against human TNF-BP I and the hybridoma cell lines (TBP-1, TBP-2, and TBP-6) which produce these antibodies.

The invention also relates to the use of tbp-1, tbp-2 and tbp-6 for detecting TNF-BP I in body fluids or cell culture media by immunoassay. This invention also relates to immunoassay kits employing tbp-1, tbp-2, tbp-6 or other antibodies for the detection of TNF-BP I in biological samples.

This invention also provides a method for increasing the protective effect of TNF-BP I against TNF-α or TNF-β.

The present invention is also drawn to the use of immobilized tbp-1, tbp-2, and tbp-6 for purifying TNF-BP I by affinity chromatography.

DETAILED DESCRIPTION OF THE PREFERRED EMBODIMENTS

Figure 1A:
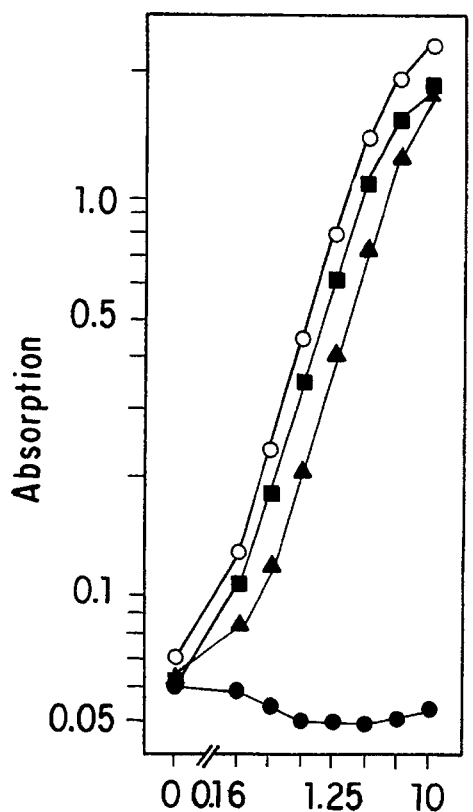
FIG. 1 (Panels A–D) depicts tour graphs showing the results of TNF-BP I ELISAs employing four different coating antibodies. Panels A–D illustrate the results obtained with tbp-1, tbp-2, tbp-6 and H398 as the coating antibodies, respectively. The symbols indicate the peroxidase conjugates of the antibodies; tpb-1 (solid circles), tbp-2 (solid squares), tbp-6 (solid triangles), H398 (open circles).
Figure 1B:
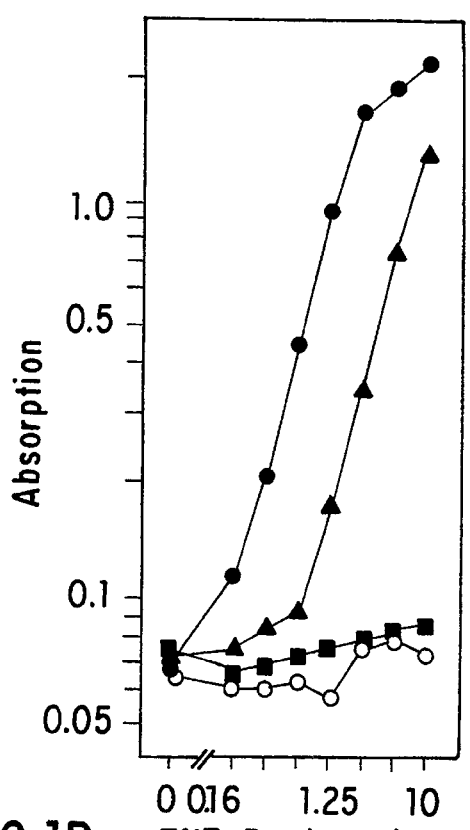
Figure 1C:
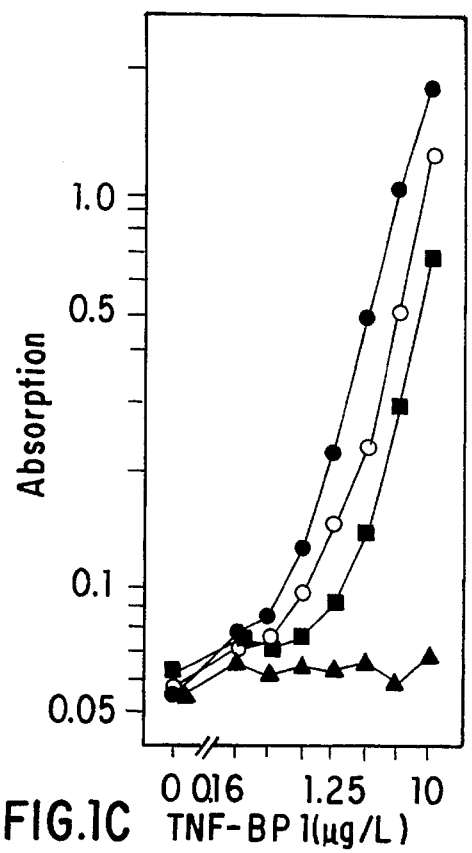
Figure 1D:
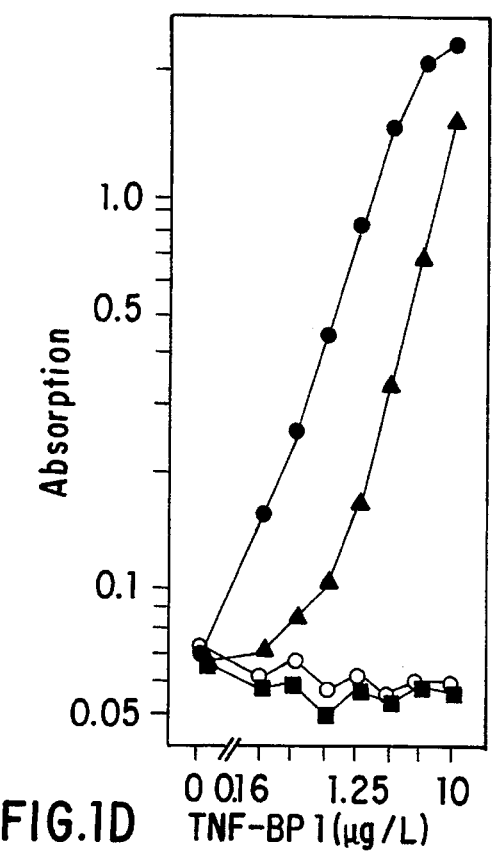

The aim of the present invention was to prepare monoclonal antibodies with specificity for human TNF-BP I, which are suitable for use in a simple and highly sensitive immunoassay for detecting TNF-BP I.

The present invention relates to monoclonal antibodies against human TNF-BP I entitled tbp-1, tbp-2 and tbp-6, active fragments thereof and the hybridoma cell lines TBP-1, TBP-2 and TBP-6 which produce these antibodies.

The hybridoma cell lines designated TBP-1 and TBP-2 were deposited on 5th Jun. 1991, and the cell line designated TBP-6 was deposited on 28th Nov. 1991 at the European Collection of Animal Cell Cultures (ECACC; Salisbury, United Kingdom) in accordance with the Budapest Agreement on the depositing of microorganisms for patent purposes (TBP-1: deposit number 91060555, TBP-2: deposit numker 91060556, TPB-6: deposit number 91112811).

The hybridoma cell lines according to the invention were obtained by immunising mice with TNF-BP I highly purified from human urine (Olsson et al., 1989) using methods known per se and spleen cells from mice with a positive antibody reaction were used for fusing with myeloma cells in order to obtain hybridoma cells which secrete monoclonal antibodies against TNF-BP I. The first cell fusion yielded two culturas which produce monoclonal antibodies against TNF-BP I; a second cell fusion yielded a third antibody-producing culture. The antibodies obtained were designated tbp-1, tbp-2 and tbp-6. The antibodies were purified and characterised: tbp-1 and tbp-6 are IgGl-antibodies whilst tbp-2 is an IgG2b-antibody. All three antibodies were capable of recognising TNF-BP I in Western blots, tbp-1 showing the strongest reactivity. tbp-2 reacted more weakly whilst tbp-6 yielded the faintest colouring. In order to characterise the epitopes which are recognised by the antibodies, the three antibodies and a fourth antibody designated H398, obtained by immunisation with solubilised TNF-receptor (Thoma et al., 1990) were investigated. The antibodies investigated recognise three different epitopes on the TNF-βP I molecule, tbp-2 and H398 recognising the same or overlapping epitopes. The sandwich ELISAs carried out in the presence of TNF-α in various arrangements with the antibodies lead one to conclude that the epitopes recognised by H398 and tbp-2 are involved in the binding of TNF-α, whilst those recognised by tbp-1 and tbp-6 are not connected to the ligand binding site. It was found, surprisingly, that some monoclonal antibodies against TNF-BP I are not only capable of binding TNF-BP I in the presence of excess TNF-α, but moreover significantly increase the protective effect of TNF-BP I against the cytotoxic activity of TNF-α and TNF-β. This effect was observed with the two antibodies tbp-1 and tbp-6. (These two antibodies belong to the group of antibodies against TNF-BP I, which do not compete with TNF-α and TNF-β for the binding of TNF-BP I. By contrast, the antibodies tbp-2 and H398, which compete with TNF-α for binding to TNF-BP I, block the activity of TNF-BP I).

According to another aspect, the present invention relates to the use of tbp-1 and/or tbp-2 for detecting TNF-BP I in body fluids or cell culture residues by immunoassay.

(The terms tbp-1 and tbp-2, in connection with the use of these antibodies, also includes hereinafter the active fragments thereof which bind to TNF-BP I. Experts in the relevant field will be familiar with methods of preparing active antibody fragments (Fab-fragments), e.g. by means of enzyme digestion.)

The present invention also relates to the use of tbp-1 and tbp-6 for detecting TNF-BP I in body fluids or cell culture residues by means of immunoassay. The antibody combination tbp-1/tbp-6 is particularly suitable for use in samples in which there are very high concentrations of TNF-α and/or TNF-β, which disrupt the measurement of TNF-BP I in other test systems.

The immunoassays which can be used within the scope of the present invention are based on standard methods with which experts in the field will be familiar and of which there are a large number available. These methods are based on the formation of a complex between the antigenic substance to be measured and one or more antibodies. One or more of the complex partners is labelled so that the antigen can be detected and/or quantitatively measured. Labelling may take the form, for example, of a coupled enzyme, radioisotope, metal chelate or a fluorescent, chemiluminescent or bioluminescent substance.

In the case of a competitive immunoassay, the antigen in the sample to be analysed competes with a known quantity of labelled antigen for binding to the antibody binding sites. The quantity of labelled antigen bound to the antibody is therefore inversely proportional to the quantity of antigen in the sample.

In tests using labelled antibodies, the quantity of labelled bound antibody is directly proportional to the quantity of antigen.

Assays based on the formation of an antibody/antigen/antibody complex, using two antibodies which do not prevent each other from binding to the antigen, are known as "sandwich" immunoassays.

Since monoclonal antibodies are available in unlimited amounts with a constant quality, immunoassays using monoclonal antibodies have crucial advantages, thanks to their constant quality and reproducibility, over assays which use polyclonal antibodies. Morever, they avoid the disadvantage connected with polyclonal antibodies, namely that animals have to be used constantly in order to produce them.

Preferably, the monoclonal antibodies according to the invention are used in a sandwich immunoassay, particularly a sandwich ELISA.

The monoclonal antibodies according to the invention can be used in sandwich immunoassays as coating- and labelling-coupled antibodies and thus make it unnecessary to use polyclonal antibodies.

According to another aspect the present invention relates to immunoassay kits, particularly sandwich immunoassay kits containing tbp-1 and/or tbp-2.

A preferred embodiment of the present invention is a sandwich immunoassay kit, preferably a sandwich ELISA kit, in which tbp-1 is the coating antibody and tbp-2 is the labelled, preferably enzyme-coupled antibody.

It is possible within the scope of the present invention, in a sandwich immunoassay, to replace tbp-1 or tbp-2 with another antibody which is capable of forming an antibody/antigen/antibody complex with tbp-2 or tbp-1.

If tbp-1 or tbp-2 is replaced by another antibody, it is preferable to use an antibody which recognises the same epitope of TNF-BP I or part thereof as the tbp-1 or tbp-2 which is to be replaced.

Sandwich immunoassays can be used to determine which antibodies are suitable as a replacement for tbp-1 or tbp-2 in the immunoassay on the basis of their ability to form an antibody/antigen/antibody complex with tbp-2 or tbp-1. Immunoassay plates are coated with tbp-1 or tbp-2, the antigen added and the labelled antibodies to be investigated applied. Antibodies which are capable of forming an antibody/antigen/antibody complex with tbp-1 or tbp-2, which can be determined by measuring the labelling of the test antibody, recognise a different epitope on the antigen from tbp-1 or tbp-2. Antibodies which are not capable of forming a sandwich with tbp-1 or tbp-2 show the same or an overlapping epitope recognition as these antibodies.

If one of the antibodies tbp-1 or tbp-2 is replaced in the sandwich immunoassay, preferably the labelling-coupled antibody tbp-2 is replaced by an antibody which has the same or overlapping epitope specificity as tbp-2. An example of a suitable antibody is the monoclonal antibody H398 described by Thoma et al. (1990), which has been shown, within the scope of the present invention, to bind to an identical or overlapping epitope.

With the help of a sandwich ELISA according to the invention based on tbp-1/tbp-2, it has been possible to detect TNF-BP I in human serum, plasma, urine and cell culture residues with a sensitivity of about 200 ng/l and an accuracy of more than 10%.

It has been found, surprisingly, that the natural ligands for the TNF-receptor, TNF-$\alpha$ and TNF-$\beta$, do not affect the predictive qualities of the immunoassay according to the invention in which tbp-1 and tbp-2 are used: TNF-$\beta$ has no measurable influence on the assay whilst TNF-$\alpha$ only causes a measurable change to the signal at concentrations of $\geq 10$ µg/l. Since the TNF-$\alpha$ concentrations in healthy people are normally $\leq 20$ ng/l and, even in serious pathological conditions, the TNF-$\alpha$ concentrations only rarely exceed 1 µg/l (e.g. Lähdevirta et al., 1988; Offner et al., 1990), falsification of the immunoassay according to the invention by endogenous TNF-$\alpha$ secreted under natural conditions can be ruled out.

In view of its sensitivity, an immunoassay based on the monoclonal antibodies tbp-1/tbp-2 is also capable of detecting concentrations of TNF-BP I which deviate downwards from the normal levels. Thus, functional disorders of the body which are accompanied by a reduced production of TNF-BP I can be detected diagnostically.

In addition to detecting TNF-BP I in serum, plasma and urine and in cell culture residues, the monoclonal antibodies tbp-1 and tbp-2 can also be used for detecting TNF-BP I in other body fluids, e.g. in cerebrospinal fluid or in broncho-alveolar secretions.

In the experiments carried out within the scope of the present invention it was found, surprisingly, that the signal obtained in a sandwich ELISA with a combination of tbp-1 and tbp-6 was not even affected by extremely high TNF-$\alpha$ or TNF-$\beta$ concentrations in the region of 10 mg/l.

The antibody combination tbp-1/tbp-6 is preferably used in a sandwich immunoassay, especially in a sandwich ELISA, whilst tbp-1 and tbp-6 may both be used as a coating antibody and as a labelled antibody.

Examples of the use of the pair of antibodies tbp-1/tbp-6 for detecting TNF-BP I include samples from in vitro experiments in which cells such as leukocytes are stimulated with lipopolysaccharides, or serum samples from experimental animals treated with large quantities of lipopolysaccharides or bacteria. Under these conditions, TNF-$\alpha$ is secreted in extremely large amounts.

Thus, with the aid of the present invention, a highly sensitive method of detecting TNF-BP I is provided, by means of which it is possible to determine the activation of the TNF receptor by its physiological ligands TNF-$\alpha$ and TNF-$\beta$ and its transmodulation by other mediators in various pathological conditions or in in vitro models. The detection of TNF-BP I in body fluids is thus particularly useful for diagnosing pathological conditions which are accompanied by an increased TNF-$\alpha$ production, or for confirming such diagnoses.

One advantage of TNF-BP I determination, as compared with TNF-$\alpha$ determination, is the fact that normal levels of TNF-BP I are found in the serum, thus making it possible to detect even slightly raised levels and thereby reach a diagnosis.

In spite of the clear correlation between the induction of TNF-$\alpha$ and the occurrence of septicaemic and endotoxaemic reactions in animals, the measurement of TNF-$\alpha$ in patients suffering from severe gram-negative infections has produced conflicting results. This would appear to be connected with the mechanisms which control the synthesis and secretion of TNF-α. When activated by a suitable stimulus, TNF-α is rapidly secreted by macrophages, after which the macrophages should be resistant to further stimulation. Moreover, the half-life in the plasma is short, being only 15 to 17 minutes in humans. These phenomena would appear to be the reason why the appearance of TNF-α in the blood system is rapid and short-lived and therefore difficult to detect (Michie et al., 1988). Therefore, if blood is not taken from the patient at the right time, it is possible that the increase in the TNF-α concentration will not be detectable at the moment of analysis. Lantz et al. (1990a) have established that, after infusion with TNF-α, the TNF-BP I level in the serum drops much more slowly than the serum TNF level. This finding indicates that the measurement of TNF-BP I concentrations as a basis for diagnosis is particularly advantageous if one is setting out to diagnose pathological conditions connected to activation of the TNF-receptor system, particularly by TNF-α, and wherein the TNF-α level falls more rapidly by comparison with the TNF-BP I level.

Examples of diseases which can be diagnosed with the aid of the measurement of TNF-BP I include gram-negative or general bacterial infections, septic shock, tissue damage in "Graft-versus-host" disease and cerebral malaria as well as cachexia.

The immunoassays according to the invention are particularly beneficial in diagnosing septic shock, which is a life threatening disease if treatment is not carried out promptly.

With the aid of an immunoassay according to the invention based on the monoclonal antibodies tbp-1 and tbp-2, TNF-BP I could be detected in the serum of normal donors at an average concentration of about 2 µg/l. Raised levels were detected in the serum of patients suffering severe burns; very high levels were detected in dialysis patients, whereas the sera of patients with chronic polyarthritis showed no increased TNF-BP I concentrations.

The immunoassays according to the invention also provide, for the first time, a simple. immunological method of detecting TNF-BP I in the urine; in urine samples from normal donors, an average TNF-BP I concentration of about 2 µg/l was detected.

The immunoassays according to the invention can thus be used to diagnose pathological conditions in which there is a correlation between raised TNF-BP I concentrations in the urine and in the serum, as was found in cases of kidney failure, by determining the concentration of TNF-BP I in the urine. This method has the advantage of requiring no blood sample and of being able to provide a diagnosis on the basis of urine analysis, which is considerably more pleasant for the patient.

The term "diagnosis", for which the immunoassays according to the invention can be used, also covers the monitoring of the course of a disease which is connected with activation of the TNF-receptor system, or the course of therapy for treating such a disease, e.g. treatment with antibodies against TNF-α. The use of the immunoassay according to the invention is also convenient for monitoring the progress of therapies in which TNF-α or TNF-β are administered. In the course of these diagnostic applications, a sample of body fluid is generally taken from the patient at regular intervals and examined for its content of TNF-BP I.

Monoclonal antibodies against TNF-BP I, which do not compete with TNF-α and/or TNF-β for binding to TNF-BP I and which increase the protective effect of TNF-BP I, may be used according to the invention to reinforce the effect of TNF-BP I within the scope of the treatment of diseases in which TNF-α and/or TNF-β has a damaging effect. (It has been found that the protective effect of TNF-BP I against TNF-α is relatively weak (Lantz et al., 1990b, Loetscher et al., 1991)).

In order to make use of the reinforcement of the protective effect of these antibodies both for endogenous TNF-BP I and also for exogenous TNF-BP I, administered therapeutically, the antibodies may be used per se or combined with TNF-BP I in suitable preparations as a therapeutic agent.

Examples of antibodies of this kind which enhance the protective effect of TNF-BP I against TNF-α and TNF-β include tbp-1 and tbp-6. The suitability of other antibodies against TNF-BP I for this purpose can be established by testing the antibodies for their effect on TNF-BP I in bioassays. The dosage of monoclonal antibodies is adjusted according to the dose of TNF-BP I and is appropriately in the range from equimolar to an approximately 100-times molar excess, based on the amount of TNF-BP I.

Another field of application of the present invention is the use of the monoclonal antibodies tbp-1, tbp-2 and tbp-6 in immobilised form for purifying TNF-BP I by affinity chromatography.

In addition, the monoclonal antibodies according to the invention, especially tbp-1, can be used for detecting TNF-BP I in immunoblots.

The invention is further illustrated by the following Examples:

EXAMPLE 1

Preparation of Monoclonal Antibodies with Specificity for Human TNF-BP I a) Immunisation 3 female BABL/c mice about 6 weeks old were immunised with TNF-BP I, purified to homogeneity, according to the method described in EP A2 393 438, in accordance with the following plan:

1st immunisation: 9 µg of TNF-BP I per mouse in complete Freund's adjuvant by intraperitoneal route 2nd immunisation: 9 µg of TNF-BP I per mouse in incomplete Freund's adjuvant, by intraperitoneal route, 3 weeks after the 1st immunisation 3rd immunisation: 9 µg of TNF-BP I per mouse in incomplete Freund's adjuvant, by intraperitoneal route, 5 weeks after the 2nd immunisation.

8 days later, serum samples were taken from the mice and investigated by sandwich ELISA for the formation of antibodies against TNF-BP I. In order to do this, TNF-BP I was bound to test plates coated with rabbit antibodies against TNF-BP I and specific antibodies were detected with peroxidase-coupled rabbit antibodies against mouse immunoglobulin. The test sera were applied in dilutions of $1:10^2$, $1:10^3$, $1:10^4$ and $1:10^5$. All three mice exhibited positive reactions (absorption more than twice the background) at dilutions up to $10^5$. The mouse with the highest titre was given a booster, about 8 weeks after the 3rd immunisation, on three successive days, with 4 µg of TNF-BP I in PBS; the spleen cells of this mouse were used the next day for fusion with hybridoma cells. A second immunisation was carried out in a similar manner, except that the mouse used was additionally given a fourth dose of TNF-BP I (15 µg) 8 months after the 3rd immunisation and was given a booster 7 weeks later.

b) Fusion:

The spleen of the mouse was removed under sterile conditions one day after the last injection, mechanically chopped up and washed with serum-free culture medium (RPMI 1640). About $10^8$ spleen cells were fused using the method of Köhler and Milstein (1975) in the presence of PEG 4000 (Merck, 40% in serum free culture medium) with about $5\times10^7$ P3X63Ag8.653 BALB/c-myeloma cells (Kearney et al., 1979). The cells were then suspended in HAT-selection medium (RPMI 1640—completed with 100 U/ml of sodium penicillin G, 50 U/ml of streptomycin and 20% FCS—with $10^{-4}$M hypoxanthine, $4\times10^{-7}$M aminopterin and $1.6\times10^{-5}$M thymidine) and distributed into 16 96-well microtitre plates containing peritoneal mouse cells as the "Feeder Layer". After 11 days, supernatants were removed and tested for antibody production. Of the 1500 cultures which were grown in selective medium, more than 90% showed growth of hybridomas.

c) Screening of hybridoma culture residues

Unless otherwise specified, the following buffers Were used for all ELISA experiments:
Coating buffer: 0.05M sodium carbonate pH 9.6 Washing medium: phosphate-buffered saline solution pH 7.4 (PBS) containing Tween 20 in an amount of 0.5 g/l Test buffer: PBS with bovine serum albumin (5 g/l) and Tween 20 (0.5 g/l) Substrate solution: tetramethylbenzidine dihydrochloride (0.1 g/l) and sodium perborate (0.05 g/l) in 0.05M potassium citrate pH 5.0
Stopping solution: 2M sulphuric acid 96-well immunoassay plates were coated with rabbit antibodies against TNF-BP I, partially purified by ammonium sulphate precipitation (50% saturation), in coating buffer at a concentration corresponding to a 1:3000 serum dilution (50 µl/well, incubation overnight at 4° C. or for one hour at 37° C.). The plates were washed once and blocked with test buffer at ambient temperature for one hour. Then hybridoma residues (50 µl) were added together with the antigen (50 µl, 10 µg TNF-BP I/l in test buffer) and the dishes were incubated for 2 hours at ambient temperature. They were washed once, a solution of peroxidase-coupled rabbit antibodies against mouse immunoglobulins (DAKO, Denmark, 1:5000 dilution in test buffer, 50 µl/well) was added and the plates were incubated for 2 hours at ambient temperature. They were then washed 3 times and 200 µl of substrate solution were added to each well. After 20 to 40 minutes the reaction was stopped by the addition of 50 µl of stopping solution. The absorption of the solution was measured in an ELISA reader at a wavelength of 450 nm (reference: 690 nm), using culture medium as the negative control and dilute mouse immune serum as positive control. Only two of the cultures investigated from the first immunisation showed any antibody production (TBP-1 and TBP-2); the second fusion yielded a third antibody-positive cell line (TBP-6). The positive cultures were transferred after about 25 days from HAT-medium into HT-medium and after a further 10 days they were transferred to normal culture medium (RPMI 1640 complete, 1% antibiotics, 10% L-glutamine, 10% FCS).

d) Cloning of the hybridomas:

The positive cultures were cloned by the limiting dilution method. Dilution was carried out so that 100 µl of culture medium contained 1 cell, after which the wells in a 96-well dish were filled with this volume (a total of 3 dishes were prepared, in which each well was charged with 100 µl of mouse peritoneal macrophage suspension on the previous day). The culture residues were tested by ELISA as described above; positive clones from each culture were pooled, expanded and frozen.

e) Production of monoclonal antibodies

In order to produce antibodies in vivo, about $10^7$ cells were taken from each hybridoma culture and injected intraperitoneally into BALB/c mice which had been treated 2 or 3 days previously with 0.5 ml of incomplete Freund's adjuvant. After about 10 to 14 days the Ascites fluid was removed. The monoclonal antibodies formed were purified by ammonium sulphate precipitation followed by affinity chromatography over carrier-bound protein-G.

For antibody production in cell culture, foetal calves' serum (FCS) was purified by chromatography on protein-G-sepharose in order to eliminate bovine IgG; this serum preparation was used in a concentration of 5% for the hybridoma cultures. The antibodies were again isolated from the culture residues using protej. n-G-sepharose. Alternatively, the cells were grown in serum-free medium (serum-free and protein-free hybridoma medium, Messrs. SIGMA, Catalogue No. 5-2772; USA) and the antibodies were likewise isolated by chromatography on protein-G-sepharose.

EXAMPLE 2

Characterisation of the monoclonal antibodies

The antibody subisotypes were determined using peroxidase-coupled rabbit antibodies (Serotec, Oxford, GB): tbp-1 and tbp-6 are IgGl-antibodies whilst tbp-2 is an IgG2b-antibody.

In the Western blot, all three antibodies recognised TNF-BP I; tbp-1 showed a strong reactivity, tbp-2 reacted less strongly whilst tbp-6 yielded only a very slight coloration.

In order to determine the epitopes which were recognised by the antibodies, the three antibodies tbp-1, tbp-2 and tbp-6 and the antibody H398 developed by Thoma et al. (1990) by immunising with solubilised TNF-receptor were coupled to horseradish peroxidase and characterised by ELISA: test plates were each coated with one of the unlabelled antibodies (10 mg/l), after which a series of dilutions of the antigen were added and then one of the enzyme coupled antibodies was applied. This experiment was carried out in every possible arrangement [FIG. 1: A: tbp-1; B: tbp-2, C: tbp-6, D: H398. The symbols indicate the peroxidase conjugates: tbp-1 (solid circles), tbp-2 (solid squares), tbp-6 (solid triangles), H398 (open circles)]. It was found that none of the individual antibody species was capable of forming a "sandwich", which indicates that the antigen is present in the form of a monomer. Combinations of the antibodies tbp-1 with tbp-2, tbp-6 or H398 and combinations of tbp-2 with tbp-6 or tbp-6 with H398 were capable of producing dosage-dependent signals, whereas tbp-2 in conjunction with H398 did not react. From this it was concluded that the antibodies recognise three different epitopes on the TNF-BP I molecule; tbp-2 and H398 bind to identical or overlapping epitopes. For further development a test arrangement was chosen in which tbp-1 constitutes the coating antibody and tbp-2 the peroxidase-coupled antibody.

EXAMPLE 3

Development of an Enzyme Linked Immunosorbent Assay (Sandwich-ELISA)

In the light of the use of ELISAs for detecting TNF-BP I in human serum, first of all various media were investigated for their suitability as dilution media for samples and a standard. Whereas both FCS and also calves' serum yielded useable dosage-activity curves, pooled normal human serum showed a very high blank value. In order to check whether this phenomenon can be put down to non-specific reactivity or to the presence of antigen, human serum was passed over an affinity column containing immobilised TNF-α. As the throughflow of the chromatography column was used as a diluting medium, the blank value was approximately equal to that obtained with calves' serum. This indicated that normal human serum contains immune-reactive and biologically active TNF-BP I. The concentration of TNF-BP I in the serum pool used was estimated at about 1 µg/l. Standard curves drawn up with 50% calves' serum could not be distinguished from those with 50% human serum from which TNF-BP I had been removed. Therefore, the former medium was used for all subsequent tests (of all the supplies of calves' serum used obtained from various companies, only two proved suitable; all the others exhibited poor reproducibility.

The tests were set up and carried out according to standard methods.

First of all, in preliminary tests for developing an assay for measuring TNF-BP I in serum, it was found that a so-called two-step assay, i.e. a method in which incubation of the sample is followed by a washing step and the incubation with the antibody-enzyme conjugate is carried out separately, has no advantage over the faster and more convenient one step method. Furthermore, preliminary tests were carried out in order to vary the concentration of the coating antibody and to vary the incubation time for the immune reaction.

The optimised assay was carried out in order to determine TNF-BP I in serum as follows: 96 well immunoassay plates were coated with the monoclonal antibody tbp-1 at a concentration of 3 mg/l in coating buffer (overnight at 4° C. or for 1 hour at ambient temperature; 100 µl/well). The wells were washed once and the binding sites remaining were blocked with 200 µl of test buffer at ambient temperature for 1 hour. After another washing cycle the wells in rows 2 and 11 were filled with 100 µl of 50% calves' serum/50% PBS. A standard solution of TNF-BP I (see Example 1a, 20 µg/l in 50% calves' serum/50% PBS, 100 µl) was pipetted into wells A2 and A11; serial dilutions in the ratio 1:2 were made directly in the wells in rows 2 and 11. All other wells were given 50 µl of PBS and the serum samples were each pipetted out twice (50 µl/well). 50 µl of a solution of peroxidase-coupled antibody tbp-2 in test buffer were placed in all the wells after a suitable dilution had been established in preliminary trials. (The coupling of the antibodies to horseradish peroxidase (Boehringer Mannheim) was carried out in accordance with the method described by Wilson and Nakane (1978)). The plates were incubated for 3 hours at ambient temperature on a plate vibrating apparatus. The plates were then washed three times, substrate solution was added (200 µl), the reaction was stopped by the addition of 50 µl of stopping solution and the absorption values were determined as described above. The concentrations of TNF-BP I in the samples were calculated using the Titercalc program (Hewlett Packard).

In a similar way an assay was set up for analysing cell culture residues, except that, when plotting the calibration curve, cell culture medium containing 10% FCS was used and the samples were used undiluted.

A modified (two step) method was developed for measuring TNF-BP I in the urine. The need for this arose because the low pH value of some samples and other unexplained factors interfered with the test. The effect caused by the pH value could not be compensated by means of the standard test buffer owing to the insufficient buffer capacity. A strong phosphate buffer (0.5M) was necessary in order to ensure that even the most acidic samples (pH 5) could be brought up to a neutral pH. This measure was still not sufficient as some samples still showed poor reproducibility. This problem was solved by using a two-step test method (successive incubation of samples and conjugate): the plates were coated, blocked and washed as described for the serum assay. Then a solution consisting of bovine serum albumin (5 g/l) and Tween 20 (0.5 g/l) in 0.5 molar sodium phosphate buffer pH 7.4 was pipetted into the wells in the plate (50 µl/well). The calibration curve was drawn up with the same solution. Then urine samples (50 µl/well; measurements carried out twice) were added and the plates were incubated for 2 hours on a vibration apparatus. The plates were then washed and 100 µl of a solution of enzyme conjugate in test buffer was added, after which incubation was carried out for a further 2 hours. The final treatment of the plates and the quantitative measurement of TNF-BP I were carried out as described above for the serum test.

Figure 2:
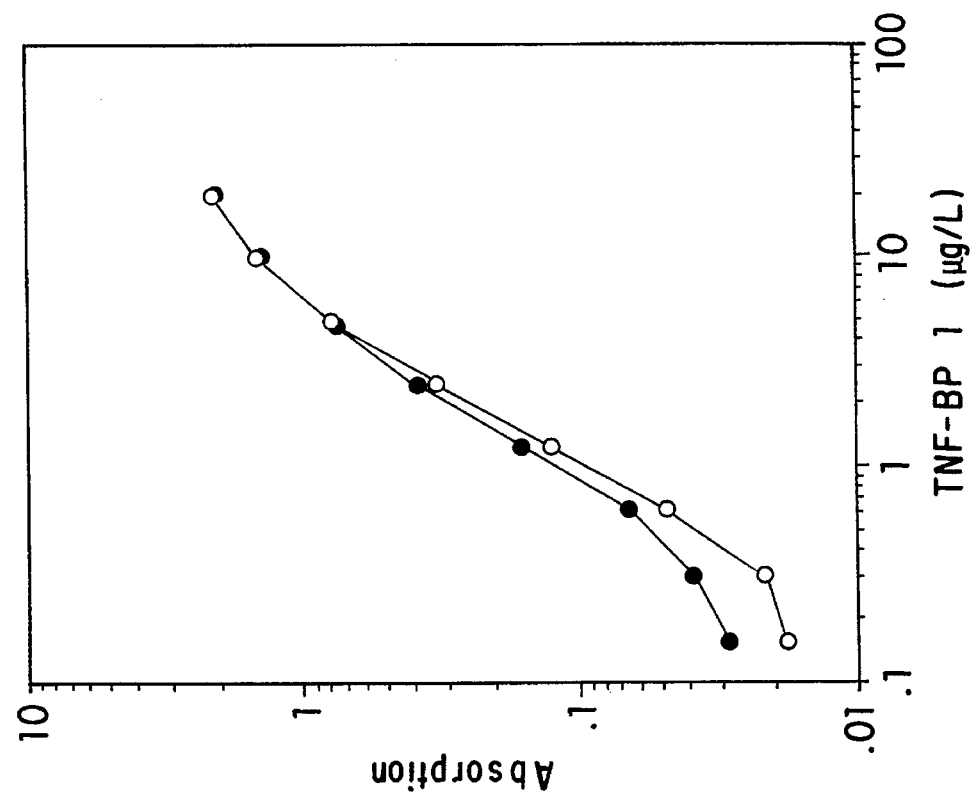
FIG. 2 depicts a graph showing calibration curves for TNF-BP I ELISAs of serum (solid circles) and urine (open circles) samples.

A typical calibration curve is shown in FIG. 2 (solid circles: serum samples; open circles: urine samples); it permits quantitative measurement of TNF-BP I in a concentration range of between 0.3 and 10 µg/l. The detectable minimum quantity in the serum, defined as the concentration which produces a signal corresponding to the blind value signal plus three standard deviations, was determined at 0.2 µg/l (average of 4 independent assays). At concentrations of up to 1 mg/l (100-fold excess compared with the normal test range) no "high-dose hook" effect (excess antigen) could be detected. The sensitivity of the test for urine samples was comparable. The sensitivity for cell culture samples is around 0.1 µg/1l since these samples are used undiluted.

The accuracy of the serum assay was tested by analysing serum samples containing TNF-BP I at concentrations of 2 and 10 µg/l in six different tests. The intra-assay variation coefficients were 4.7% and 5.9%, respectively; the inter-assay variation coefficients were 6.6% and 7.5%, respectively. The linearity was determined by investigating a series of external two-fold dilutions of TNF-BP I in the serum (concentrations between 0.3 and 10 µg/l) and the linear regression of the values determined experimentally was calculated by comparison with the expected values. In three independent tests, correlation coefficients of between 0.998 and 1 were obtained.

The detection of TNF-BP I by serum assay was investigated by adding exogenous TNF-BP I to the serum of 7 normal donors in two different concentrations (1 and 5 µg/l). This experiment was made more difficult by the fact that all the samples contained endogenous TNF-BP I in various concentrations; these values therefore had to be subtracted before the detection rate could be calculated. The average detection rate was found to be 83±15% at 1 µg/l and 85±13% at 5 µg/l (range: 62–101% and 65–105%, respectively).

The detection of TNF-BP I by means of the modified urine assay in 14 urine samples to which exogenous TNF-BP I was added was investigated in the same way as for the serum samples; the average detection rate for a nominal concentration of 5 µg/l was 83±15% (range: 52–104%).

Figure 3:
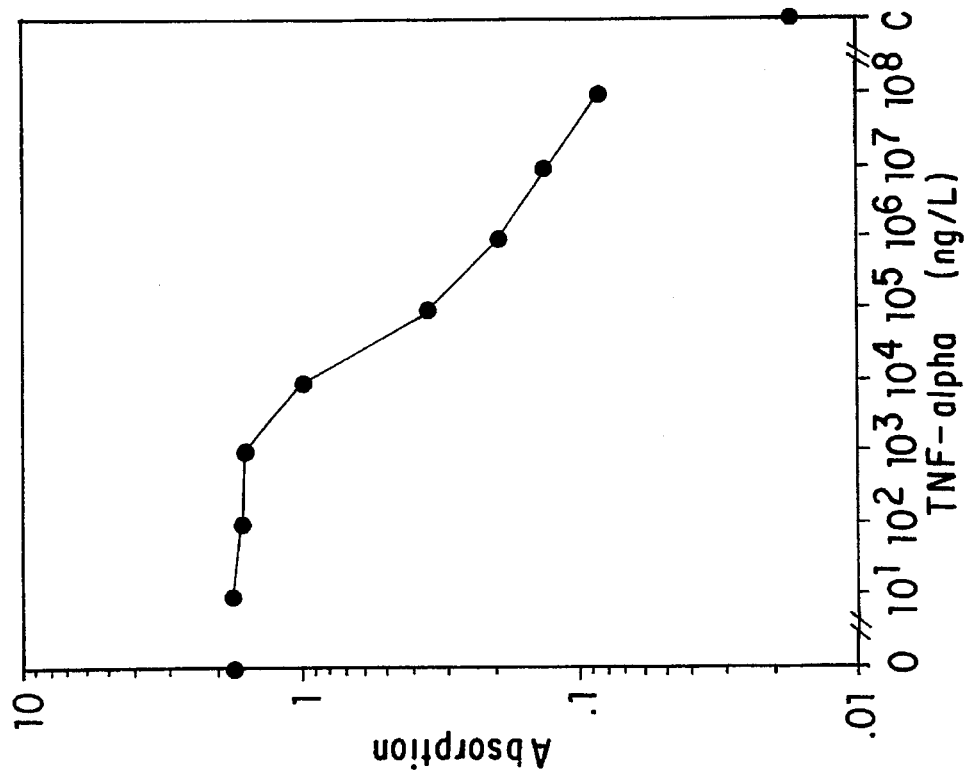
FIG. 3 depicts a graph showing the effect of increasing concentrations of TNF-α on the immunoreactivity of TNF-BP I.

In order to determine whether the physiological ligands of the TNF-receptor influence the interaction of TNF-BP I with the antibodies, the ELISA was carried out at a constant concentration of TNF-BP I (5 µg/l) in the presence of increasing concentrations of recombinant TNF-α (Gray et al., 1984) and recombinant TNF-β (Pennica et al., 1984), in each case from *E. coli* and with a purity of >99%. As can be seen from FIG. 3 (C shows the assay background in the absence of TNF-BP I), TNF-α inhibits the reactivity of TNF-BP I with the antibodies at concentrations ≦10 µg/l; by contrast, TNF-α exhibited no activity even at very high concentrations (up to 100 mg/l).

EXAMPLE 4

Stability of TNF-BP I a) Stability in the serum

Filter-sterilised samples of pooled normal serum were stored for 24 hours at various temperatures; the samples were also subjected to several freezing/thawing cycles. As can be seen from Table 1, neither the incubation at temperatures of 37° C. nor the repeated freezing and thawing affected the immune reactivity of TNF-BP I. The samples consisted of pooled human serum containing endogenous TNF-BP I (sample 1:1.2 µg/l) and the same serum sample with the addition of exogenous TNF-BP I (sample 2: final concentration 5 µg/l).

b) Stability in the urine

The tests were carried out as specified under a); three samples were investigated which represented a broad spectrum of pH values. As can be seen from Table 1, TNF-BP I was stable in all the samples after freezing and thawing. All the samples could be stored for 24 hours at temperatures up to 37° C. without losing any activity. The urine samples originated from three different donors (sample 1: pH 5.1, 1.9 µg/l; sample 2: pH 5.9, 4.0 µg/l; sample 3: pH 7.2, 3.7 µg/l). "nd" indicates "not determined".

EXAMPLE 5

Detection of TNF-BP I in Human Serum

Figure 4:
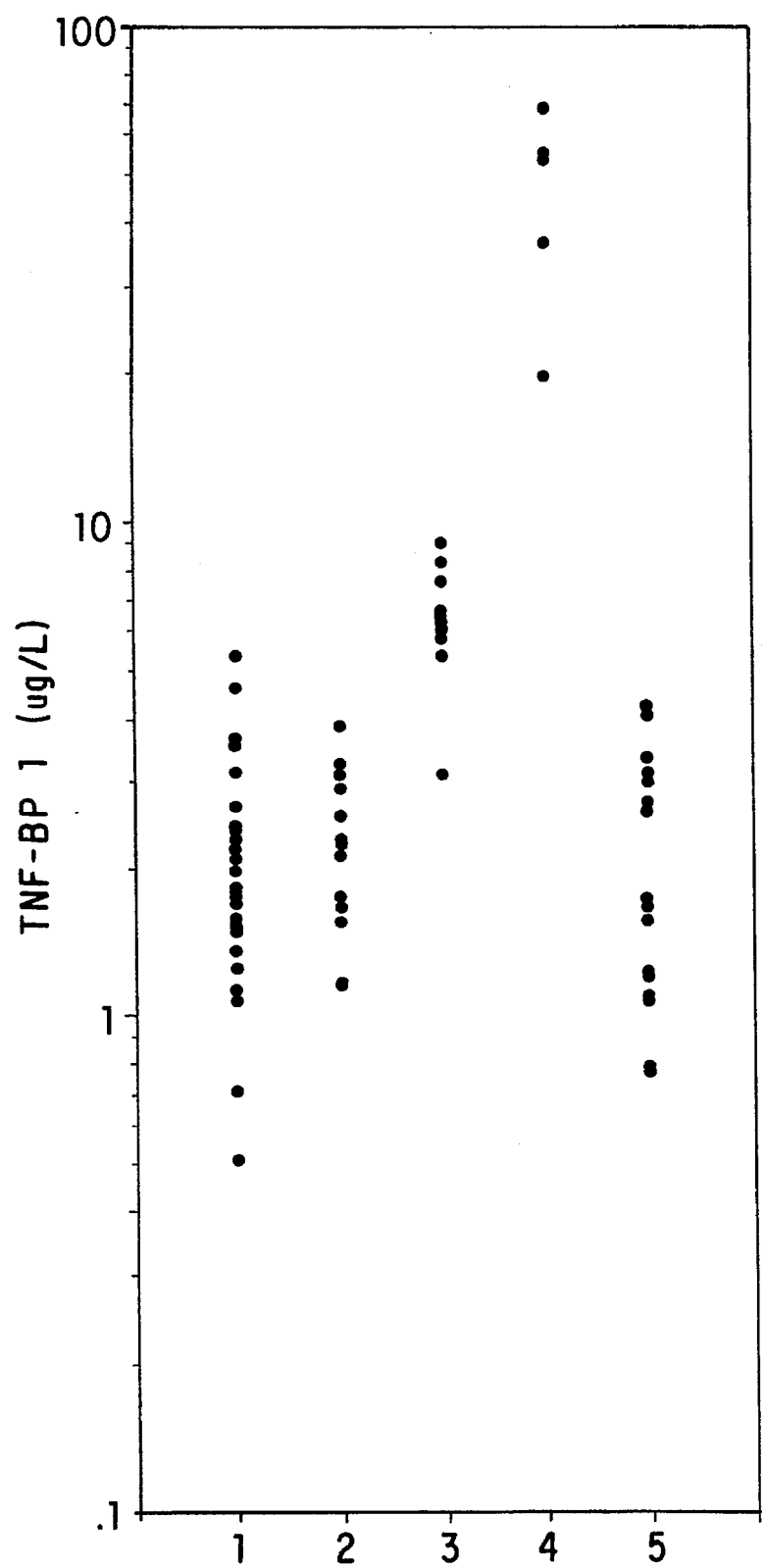
FIG. 4 depicts a graph showing the TNF-BP I concentrations in human serum and urine samples, as determined by the sandwich ELISA described in Example 3. Lane 1 represents serum samples obtained from healthy donors; lane 2, serum samples from patients with chronic polyarthritis; lane 3,serum from burn patients; lane 4, serum from patients with kidney failure; lane 5, urine samples from healthy donors.
Figure 5A:
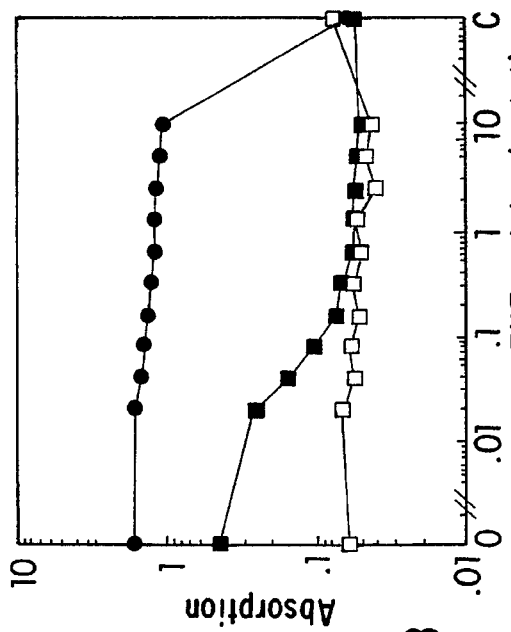
FIG. 5 (Panels A–D) depicts four graphs showing the effect of increasing concentrations of TNF-α on the TNF-BP I sandwich ELISA described in Example 3. Panels A–D show the results obtained with tbp-1, tbp-2, tbp-6 and H398 as the coating antibodies, respectively. The symbols represent the peroxidase conjugates of the antibodies; tpb-1 (solid circles), tbp-2 (open circles), tbp-6 (solid rectangles), H398 (open rectangles).
Figure 5B:
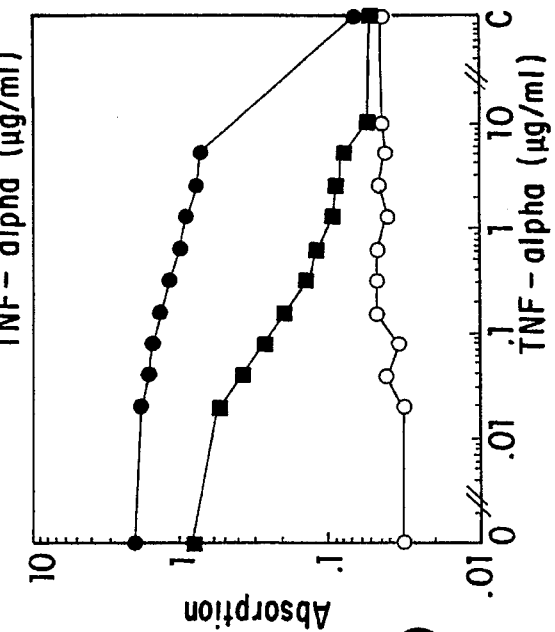
Figure 5C:
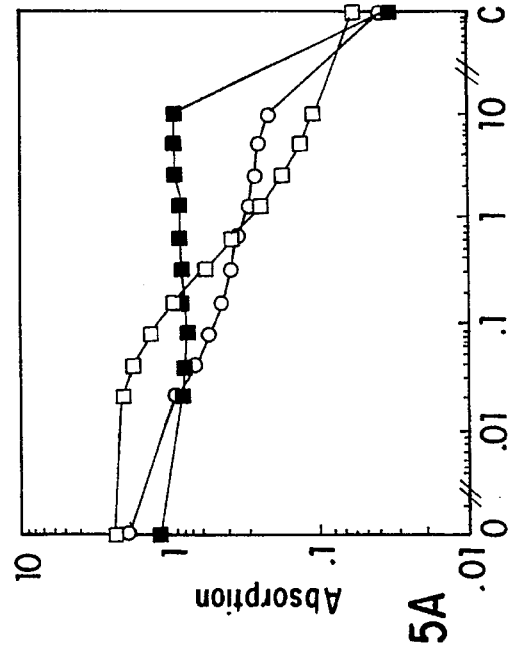
Figure 5D:
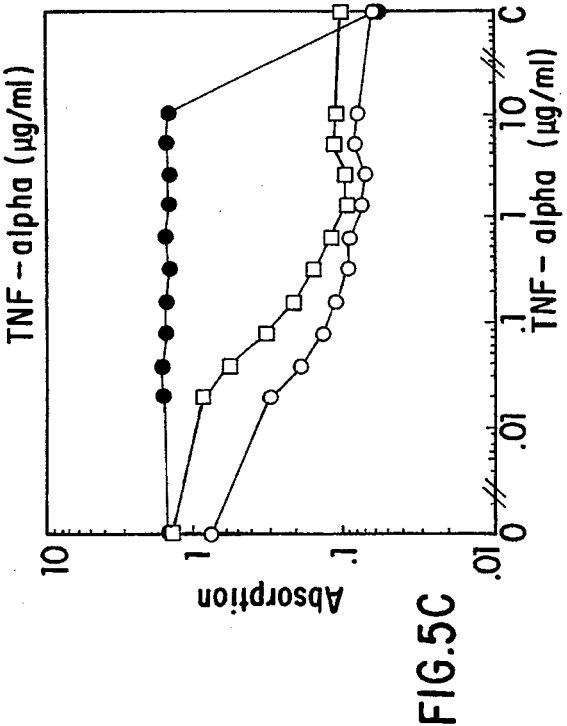

Sera from 42 normal donors (blood donors and laboratory staff) were investigated using the serum sandwich ELISAs described in Example 3. TNF-BP I concentrations varied between 0.5 and 5.4 µg/l, with an average of 2.1 µg/l (standard deviation 1.0 µg/l; FIG. 4). Serum, EDTA-plasma, citrate plasma and heparin plasma obtained at the same time, were available from two people; the TNF-BP I concentrations did not differ significantly (donor A: 1.7, 2.0, 1.6 and 1.9 µg/l; donor B: 1.8, 1.8, 1.8 and 1.9 µg/l). The TNF-BP I concentrations in sera from 15 patients with chronic polyarthritis did not differ significantly from those of healthy people (2.3±0.79 µg/l; range: 1.2–3.9 µg/l). Significantly raised levels were found in sera from patients with severe burns (6.5±1.7 µg/l; range: 3.1–9.1 µg/l; n=10). Patients with kidney failure (n=6) showed remarkably high concentrations in a range from 20–69 µg/l (average±standard deviation: 49±17 µg/l).

EXAMPLE 6

Using the sandwich ELISA developed in Example 3 specifically for urine samples, the TNF-BP I concentrations of urine samples from 16 normal donors were determined. They varied between 0.78 and 4.3 µg/l (average±standard deviation: 2.2±1.2 µg/l). There was no significant difference between female (2.1±1.4 µg/1; n=9) and male (2.2±1.0 µg/l; n=7) donors.

EXAMPLE 7

Determination of TNF-BP I in Culture Residues from Human Cell Lines

In order to determine whether the developed ELISA is suitable for detecting TNF-BP I produced by human cell cultures, a series of cell lines were investigated. Culture media (containing 10% FCS) were harvested from dense cultures, generally several days after dilution with fresh medium or after the passage of adhering cells. Culture medium containing 10% FCS was used as the standard diluent; the assays were carried out by the one-step method. TNF-BP I was detectable in residues of the cell lines A549 (lung cancer; 1.1 µg/l), HeLa (cervical cancer; 0.38 µg/l) and Namalwa (Burkitt's lymphoma; 0.25 µg/l), but was below the detection limit (100 ng/l) in the cell lines U937 (histiocyte lymphoma), EoL-3 (eosinophilic leukaemia), Raji (Burkitt's lymphoma), HL-60 (myeloid leukaemia), U266 (myeloma) and LuKII (B-lymphoblastoid cell line, immortalised by Epstein-Barr virus). In accordance with earlier results (Lantz et al., 1990b), it was observed that HL-60 cells cultivated in the presence of TNF-β (10 µg/l) released increased quantities of TNF-BP I; after 4 days of this treatment a concentration of 0.45 µg/l was achieved.

EXAMPLE 8 a) Determining the influence of TNF-α on the binding of the antibodies to TNF-BP I In order to determine whether TNF-α affects the binding of the antibodies to TNF-BP I, a one-step sandwich ELISA was carried out in a number of different arrangements. One of the monoclonal antibodies was used as a coating antibody for mopping up the antigen, a constant quantity of TNF-BP I was used in the presence of various concentrations of TNF-α, and a second monoclonal antibody labelled with horseradish peroxidase was used. The ELISAs were carried out substantially as described in Example 3: the plates were coated with 10 µg/ml of antibody in coating buffer, washed and blocked with test buffer. The one-step incubation with TNF-BP I in a final concentration of 5 ng/ml (in the presence of varying concentrations of TNF-α) and with peroxidase-coupled antibody was carried out in test buffer at ambient temperature for 3 hours. The plates were then washed, developed with substrate solution, then the reaction was stopped and absorption was measured at 450 nm in a plate reader, subtracting the absorption at 690 nm. The results of these experiments are given in FIG. 5: Panels A to D show the results of plates which were coated with the antibodies tbp-1, tbp-2, tbp-6 and H398; the symbols represent the peroxidase conjugates of the antibodies tbp-1 (solid circles), tbp-2 (open circles), tbp-6 (solid rectangles) and H398 (open rectangles); the background signal (absence of TNF-BP I) is shown at C. It was found that the signal obtained with combinations of the antibodies tbp-1 and tbp-6 was not even affected by the highest TNF-α concentrations tested (10 µg/ml). By contrast, all the combinations containing tbp-2 or H398 were sensitive to TNF-α, although with different dosage-activity ratios. (These results indicate that H398 and tbp-2 recognise epitopes which are connected with the TNF-α binding site, whereas tbp-1 and tbp-6 define epitopes which are independent thereof.)

b) Determining the influence of TNF-β on the binding of the antibodies to TNF-BP I The assay was carried out with the monoclonal antibodies tbp-1 and tbp-6 for TNF-β, as described in a). In the case of TNF-β, also, it was found that concentrations of 10 μg/ml do not interfere with the assay.

EXAMPLE 9

Cytotoxic Bioassay for Determining the Biological Activity of the Monoclonal Antibodies a) Influence of the antibodies on the protective effect of TNF-BP I against TNF-α

The cytotoxic activity of TNF-α was determined essentially using the method described by Kramer and Carver, 1986. For this purpose, mouse L-M cells (ATCC CCL 1.2) were cultivated overnight in microtitre plates, TNF-α preparations were added in serial two-fold dilutions and actinomycin D was added to give a final concentration of 1 μg/ml. The plates were incubated at 39° C. for 18 to 20 hours, the cells were stained with 0.5% crystal violet and absorption was determined at 540 nm. (The cell controls and blank values were provided 4-fold on each plate). By definition, a solution which kills off 50% of the cells contains 1 unit/ml. Under the assay conditions, the specific activity of the recombinant human TNF-α used was $5 \times 10^7$ units/mg of protein; the reference preparation for TNF-α, 86/659 (NIBSC, England) with a fixed activity of $4 \times 10^4$ E/ml, showed an activity of $5 \times 10^4$ E/ml. The neutralisation assays were carried out by pre-incubating serial dilutions of TNF-BP I in culture medium with a constant quantity of TNF-α (final concentration 20 E/ml) and/or monoclonal antibodies for 1 hour at 37° C. Then the culture liquid was removed from the plate and the pre-incubated TNF-α/TNF BP I/antibody solution was added to the cells in a quantity of 100 μl. The plates were incubated and stained as described above. TNF-BP I concentrations exhibiting a 50% protective effect on the cells (ED50) were determined graphically. The results of the bioassay carried out are given in FIG. 6; the symbols indicate the following results: TNF-BP I on its own (solid circles; broken line), TNF-BP I combined with the antibodies at 0.01 μg/ml (open triangle), 0.1 μg/ml (solid triangles), 1 μg/ml (open rectangles), 10 μg/ml (solid rectangles) or 100 μg/ml (open circles).

It was found that, in the presence of a constant quantity of TNF-α (400 pg/ml corresponding to 20 cytotoxic units/ml) half-maximum protection is obtained at TNF-BP I concentrations of 270±44 ng/ml (average of 6 independent tests). When the monoclonal antibody tbp-2 was added together with TNF-BP I (FIG. 6B), the protective effect of TNF-BP I was reduced: at antibody concentrations of 1, 10 or 100 μg/ml, the concentrations of TNF-BP I required for half-maximum protection increased to 380, 1,000 and 12,000 ng/ml, respectively. H398 reduced the protective effect of TNF-BP I to a similar degree (final values of 840, 3,800 and >20,000 ng/ml). (The treatment of the cells with these antibodies in amounts of up to 100 μg/ml in the absence of TNF did not produce any cytotoxic activities of any kind; it was also found that the antibodies do not protect the cells against the toxicity of TNF in the absence of TNF-BP I.)

Figure 6A:
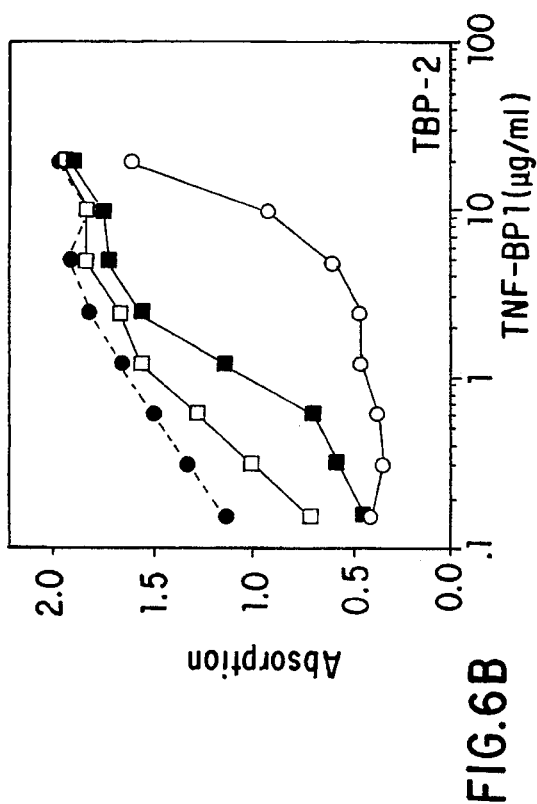
FIG. 6 (Panels A–D) depicts graphs showing the effect of monoclonal antibodies on the protective effect of TNF-BP I in a cytotoxic bioassay. Panels A–D show the results obtained with antibodies tbp-1, tbp-2, tbp-6 and H398, respectively. The solid circles represent TNF-BP I alone; open rectangles represent TNF-BP I in the presence of 1 μg/ml of the indicated antibody; the solid rectangles represent TNF-BP I in the presence of 10 μg/ml of the indicated antibody; and open circles represent TNF-BP I in the presence of 100 μg/ml of the indicated antibody.
Figure 6B:
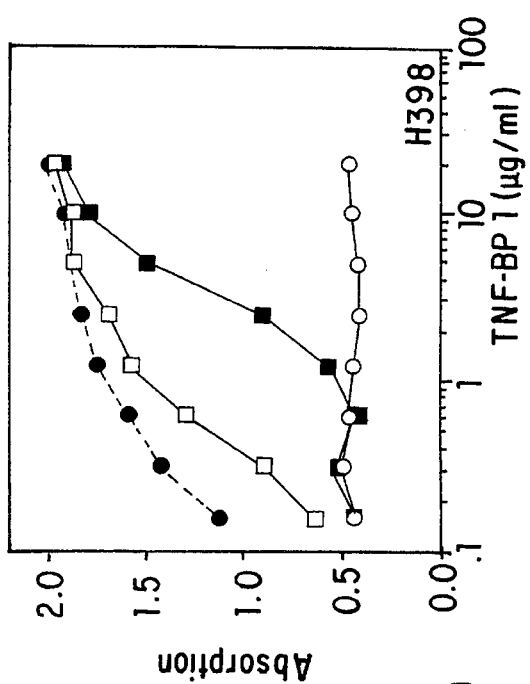
Figure 6C:
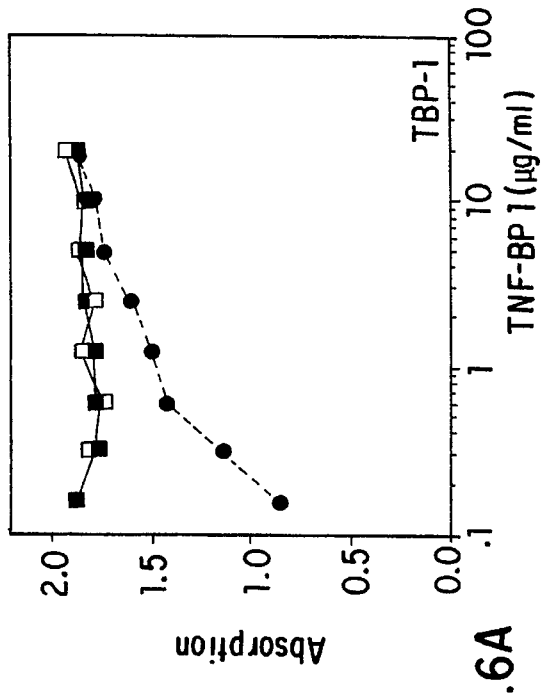
Figure 6D:
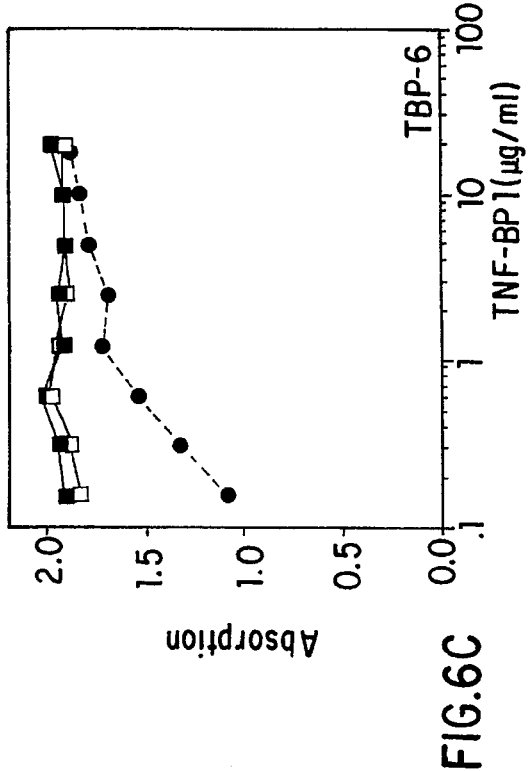

Surprisingly, however, the antibody tbp-1 did increase the protective effect of TNF-BP I (FIG. 6A). At antibody concentrations of up to 100 ng/ml, the cells were completely protected by TNF-BP I at doses as low as 40 ng/ml. tbp-6 showed a similar but quantitatively smaller activity (FIG. 6C) (this antibody also showed a lower activity in the ELISAs and presumably has a lower affinity). In the presence of a large excess of antibody (10 μg/ml) half-maximum protection could be found at a TNF-BP I concentration of 7.3±0.5 ng/ml (tbp-1) or 53±13 ng/ml (tbp-6), corresponded to an approximately 40-fold or 5-fold increase in the protective effect (which was established by titrations carried out in 4 experiments). In control tests which were carried out at the same TNF-α concentration but in the absence of TNF-BP I, the antibodies showed no activity.

b) Influence of the antibodies on the protective effect of TNF-BP I against TNF-β

In the bioassay with L-M cells carried out as described in a), the cytotoxic activity of TNF-β is greater than that of TNF-α (300 E/ng as against 50 E/ng). TNF-BP I also exhibited an inhibition of the cytotoxic effect against the same cytotoxic dose of TNF-β (20 E/ml, corresponding to 66 pg/ml), but the dosages required were at least ten times as great (ED50=3,800 ng/ml, compared with 270 ng/ml for TNF-α). The addition of the antibodies tbp-1 and tbp-6 (10 μg/ml) intensified the protective effect to a similar extent as for TNF-α; a half-maximum protective effect was achieved at 53 ng/ml and 500 ng/ml, respectively.

TABLE 1

| Stability of TNF-BP I in serum and urine | | | | | |
|---|---|---|---|---|---|
| | Treatment Serum | | % Detection Urine | | |
| | Sample 1 | Sample 2 | Sample 1 | Sample 2 | Sample 3 |
| Storage at | | | | | |
| −20° C. | 100 | 100 | 100 | 100 | 100 |
| +4° C. | 98 | 100 | 97 | 105 | 105 |
| +20° C. | 100 | 98 | 100 | 112 | 109 |
| +37° C. | 98 | 91 | 110 | 107 | 89 |
| Freezing/ thawing cycles | | | | | |
| 0 | 100 | 100 | 100 | 100 | 100 |
| 1 | 101 | 105 | 99 | 92 | 101 |
| 3 | 95 | 103 | 107 | 98 | 99 |
| 5 | 92 | 104 | nd | 94 | 99 |

BIBLIOGRAPHY:

Beutler B., 1988, Am. J. Med. 85, 287–288

Beutler B. and Cerami A., 1989, Ann. Rev. Immunol. 7, 625–655

Brockhaus M. et al., 1990, Proc. Natl. Acad. Sci. USA 87, 3127–3131

Engelmann H. et al., 1989, J. Biol. Chem. 264, 11974–11980

Engelmann H. et al., 1990 a, J. Biol. Chem. 265, 1531–1536

Engelmann H. et al., 1990 b, J. Biol. Chem. 265, 14497–14505

Gray P. W. et al., 1984, Nature 312, 721–724

Himmler A. et al., 1990, DNA Cell Biol. 9, 705–715

Kearney J. F. et al., 1979, J. Immunology 123, 1548–1550

Köhler G. and Milstein C., 1975, Nature 265, 495–497

Kohno T. et al., 1990, Proc. Natl. Acad. Sci. USA 87, 8331–8335

Kramer, S. M. and Carver, M. E., 1986, J. Immunol. Meth. 93, 201–206

Lähdevirta J. et al., 1988, Am. J. Med. 85, 289–291

Lantz M. et al., 1990 a, Cytokine 2, 1–5

Lantz M. et al., 1990 b, J. Clin. Invest. 86, 1396–1402

Loetscher H. et al., 1990, Cell 61, 351–359

Loetscher H. et al., 1991, J. Biol. Chem. 266, 18324–18329

Michie H. R. et al., 1988, J. Medicine 318, 1481–1486

Offner F. et al., 1990, J. Lab. Clin. Med. 116, 100–105

Olsson I. et al., 1989, Eur. J. Haematol. 42, 270–275

Paul N. L. and Ruddle., 1988, Ann. Rev. Immunol. 6, 407–438

Peetre C. et al., 1988, Eur. J. Haematol. 41, 414–419

Pennica D. et al., 1984, Nature 312, 724–728

Schall T. J. et al., 1990, Cell 61, 361–370

Seckinger P. et al., 1988, J. Exp. Med. 167, 1511–1516

Smith C. A. et al., 1990, Science 248, 1019–1023

Thoma B. et al., 1990, J. Exp. Med. 172, 1019–1023

Wilson M. B. and Nakane P. K., 1978, Immunfluorescence and Related Staining Techniques, Elsevier-North Holland, Amsterdam, 215–224

I claim:

1. A monoclonal antibody tbp-1or tbp-6 or an epitope binding fragment thereof which is immunoreactive with human TNF-BP I, wherein said antibody tbp-1 is produced by hybridoma TBP-1 (ECACC 91060555) and wherein said antibody tbp-6 is produced by hybridoma TBP-6 (ECACC 91112811).

2. The hybridoma cell line TBP-1 or TBP-6 deposited at the ECACC under deposit numbers 91060555 and 91112811, respectively.

3. A process for determining the amount of TNF-BP I in a sample, comprising (a) bringing said sample into contact with a monoclonal antibody or fragment according to claim 1; and (b) measuring the amount of the binary complex formed between the TNF-BP I contained in the sample and the monoclonal antibody or fragment, wherein the amount of binary complex is directly proportional to the amount of TNF-BP I present in the sample.

4. A process for determining the amount of TNF-BP I in a sample, comprising (a) bringing said sample into contact with a first antibody which is an antibody according to claim 1 and a second antibody which is detectably labeled and is immunoreactive with TNF-BP I, wherein said second antibody binds a different epitope on TNF-BP I than said first antibody; and (b) measuring the amount of the labeled ternary complex formed between the TNF-BP I contained in the sample and said first and said second antibody, wherein the amount of labeled ternary complex formed is directly proportional to the amount of TNF-BP I in the sample.

5. The process of claim 4, wherein said first antibody is tbp-1 and said second antibody is tbp-2, produced by the hybridoma TBP-2 which has been deposited at the ECACC under deposit number 91060556.

6. The process of claim 3 or 4, wherein the sample is a body fluid.

7. The process of claim 6, wherein the body fluid is serum.

8. The process of claim 6, wherein the body fluid is plasma.

9. The process of claim 6, wherein the body fluid is urine.

10. The process of claim 3 or 4, wherein the sample is cell culture medium.

11. A method for determining the amount of TNF-BP I in a sample, comprising (a) bringing said sample into contact with a carrier-bound monoclonal antibody comprising a monoclonal antibody according to claim 1, bound to a carier to form a carrier phase comprising said carrier-bound monoclonal antibody bound to said TNF-BP-I;

bringing the complex formed in step (a) into contact with a detectable antibody which forms an antibody/antigen/antibody detectable complex with said carrier-bound monoclonal antibody bound to said TNF-BP I;

(c) removing all the unbound detectable antibody from the carrier phase; and (d) measuring the amount of the detectable complex bound to the carrier phase, wherein the amount of said detectable complex is directly proportional to the amount of TNF-BP I present in the sample.

12. The method of claim 11, wherein said detectable antibody is tbp-2, produced by the hybridoma TBP-2 which has been deposited at the ECACC under deposit number 91060556 and which has been detectably labeled.

13. The method of claim 11, wherein said detectable antibody is an enzyme coupled antibody.

14. A process to aid in diagnosing a pathological condition of the human body which is characterized by reduced levels of TNF-BP I in a body fluid, comprising a) measuring the concentration of TNF-BP I in a body fluid according to the method of claim 11; and b) comparing the concentration so measured to the normal concentration of TNF-BP I in the body fluid of a human;

wherein a reduced concentration of TNF-BP I is correlated to the presence of said pathological condition.

15. The process of claim 14, wherein in said pathological condition, the TNF-α concentration in the human falls more rapidly than the TNF-BP I concentration.

16. The process of claim 14, wherein the pathological condition is septic shock.

17. The process of claim 14, wherein the body fluid is serum.

18. The process of claim 14, wherein the body fluid is plasma.

19. A sandwich immunoassay kit for determining the amount of TNF-BP I in a sample, comprising a first container containing a carrier-bound antibody which is immunoreactive with TNF-BP I; and a second container containing an antibody which is immunoreactive with TNF-BP I and is detectaby labeled, wherein said first container contains a monoclonal antibody or fragment according to claim 1, and wherein said second container contains the detectably labeled antibody which forms an antibody/antigen/antibody ternary complex with said monoclonal antibody and TNF-BP I.

20. A sandwich immuneassay kit of claim 19, comprising a first container containing tpb-1 and a second container containing tbp-2produced by the hybridoma TBP-2, which has been deposited at the ECACC under deposit number 91060556, wherein tpb-1 is bound to a solid carrier and tbp-2 possesses a detectable label.

21. A sandwich immunoassay kit of claim 19, wherein said second container contains tbp-1, wherein tbp-1 possesses a detectable label.

22. The sandwich immunoassay kit of claim 19, wherein said first container contains tpb-1 and wherein said second container contains an antibody which binds to the same or an overlapping epitope of TNF-BP I as tbp-2 produced by the hybridoma TBP-2, which has been deposited at the ECACC under deposit number 91060556.

23. The sandwich immunoassay kit of claim 19, wherein said second container contains an antibody which binds to the same or an overlapping epitope of TNF-BP I as tpb-1.

24. A process for determining the mount of TNF-BP I in a sample, comprising
   a) bringing said sample into contact with detectably labeled tpb-1 and tbp-6, wherein said tpb-1 and tbp-6 have been deposited at the ECACC under deposit numbers 91060555 and 91112811, respectively; and
   b) measuring the formation of labeled, ternary complex between the TNF-BP I contained in the sample and tpb-1 and tbp-6,
   wherein the amount of labeled complex is directly proportional to the amount of TNF-BP I in the sample.

25. A process to aid in diagnosing pathological conditions of the human body which are characterized by reduced levels of TNF-BP I in a body fluid, comprising
   a) measuring the concentration of TNF-BP I in a body fluid according to the method of claim 3; and
   b) comparing the concentration so measured to the normal concentration of TNF-BP I in the body fluid of a human;
   wherein a reduced concentration of TNF-BP I is correlated to the presence of said pathological conditions.

26. A process to aid in diagnosing pathological conditions of the human body which are characterized by elevated levels of TNF-BP I in a body fluid, comprising
   a) measuring the concentration of TNF-BP I in a body fluid according to the method of claim 3; and
   b) comparing the concentration so measured to the normal concentration of TNF-BP I in the body fluid of a human;
   wherein an elevated concentration of TNF-BP I is correlated to the presence of said pathological conditions.

27. A process to aid in diagnosing pathological conditions of the human body which are characterized by elevated concentrations of TNF-BP I in a body fluid, comprising
   (a) measuring the concentration of TNF-BP I in a body fluid according to the method of claim 11; and
   (b) comparing the concentration so measured to the normal concentration of TNF-BP I in the body fluid of a human;
   wherein an elevated concentration of TNF-BP I is correlated to the presence of said pathological conditions.

* * * * *